United States Patent [19]
Bartlett et al.

[11] Patent Number: 5,480,124
[45] Date of Patent: Jan. 2, 1996

[54] VACUUM TUBING VALVE

[75] Inventors: Bruce K. Bartlett, Santa Cruz; Fritz Haas, Novato, both of Calif.

[73] Assignee: Vision Medical and Dental, Ben Lomond, Calif.

[21] Appl. No.: 347,816

[22] Filed: Nov. 30, 1994

[51] Int. Cl.$^6$ ........................................................ F16K 5/04
[52] U.S. Cl. ............................................ 251/309; 251/304
[58] Field of Search .................................... 251/304, 309, 251/315.06

[56] References Cited

U.S. PATENT DOCUMENTS 2,189,502  2/1940  Johnston ................................. 251/309

FOREIGN PATENT DOCUMENTS 767377  1/1957  United Kingdom ..................... 251/309

*Primary Examiner*—John C. Fox
*Attorney, Agent, or Firm*—Thomas E. Schatzel

[57] ABSTRACT

A vacuum tubing valve including a first receiver tube shoulder including a tubular aperture extending along a longitudinal axis for receiving a first tubular hose. Connecting the shoulder is a stator unit including a C-shaped cavity with an opening about the side opposite the curved C-shaped wall and two apertures within the C-shaped wall and in axial alignment along the longitudinal axis. A 10 second receiver tube shoulder and tubular aperture extend along the longitudinal axis joining the stator about the second aperture. The stator includes a C-shaped rotor positioned and rotatable within the cavity, and having an elongated channel extending end-to-end. The channel is in alignment along the longitudinal axis with the first and second apertures when the rotor is in a first position, and the channel is off-set from the longitudinal axis when the rotor is in a second position. The rotor includes a frontal wall protruding from the opening to the cavity such that the rotational position of the rotor within the cavity is controllable by pressure applied to the frontal wall.

20 Claims, 1 Drawing Sheet

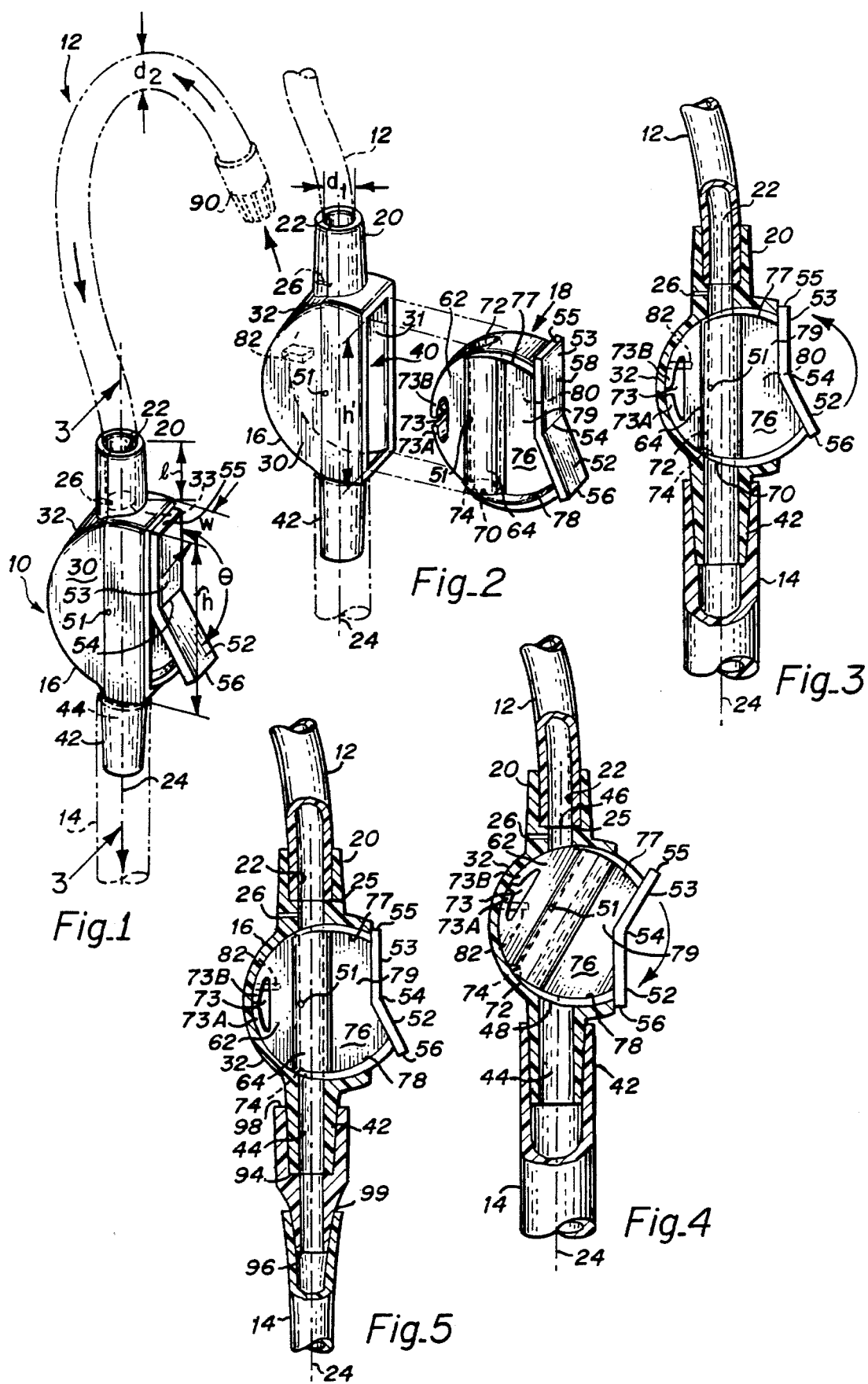

VACUUM TUBING VALVE

BACKGROUND OF THE INVENTION

1. Field of the Invention

This invention relates generally to a vacuum tubing valve, and more particularly to a conventional vacuum tubing hose utilized by dentists to extract saliva and debris from a human being's mouth. The valve attaches to the vacuum hose and contains adjustment means to eliminate the air vacuum inside the human being's mouth.

2. Description of the Prior Art

In dentistry, it is often necessary to utilize a saliva ejector instrument to extract excess saliva and debris from a patient's mouth. This extraction is necessary to create a clean, dry field of work which enhances the likelihood of success of the dentist's work.

The saliva ejector is a tube positioned within the patient's mouth containing a pulling force through the tube to a vacuum means. Although the tip of the saliva ejector which is positioned inside the patient's mouth is sterile and disposable, the hose and associated valving attached to the tip is neither. Bacteria can survive inside the hose and valving and flow back into a patient's mouth. When a patient's lips are closed around the saliva ejector's tip a seal is created that causes a backflow. Such backflow can transfer bacteria which survived inside the tube due to previous patients' to the current patient. Thus, there is a need for an economical disposable valve which eliminates undesirable backflow.

SUMMARY OF THE PRESENT INVENTION

It is therefore an object of the present invention to provide a vacuum tubing valve which is inexpensive to manufacture.

Another object of the present invention is to provide a vacuum tubing valve which is disposable.

Another object of the present invention is to provide a vacuum tubing valve which prevents undesirable backflow.

Another object of the present invention is to provide a vacuum tubing valve for use in medical and/or dental operations which assists in preventing transmission of bacteria, diseases and viruses to a patient.

Another object of the present invention is to provide a vacuum tubing valve which is easy to manufacturer.

Another object of the present invention is to provide a vacuum tubing valve which can be easily manufactured and assembled.

Briefly, a preferred embodiment of the present invention includes a vacuum tubing valve including a first receiver tube shoulder including a tubular aperture extending along a longitudinal axis for receiving a first tubular hose. Connecting the shoulder is a stator unit including a C-shaped cavity with an opening about the side opposite the curved C-shaped wall and two apertures within the C-shaped wall and in axial alignment along the longitudinal axis. A second receiver tube shoulder and tubular aperture extend along the longitudinal axis joining the stator about the second aperture. The stator includes a C-shaped rotor positioned and rotatable within the cavity, and having an elongated channel extending end-to-end. The channel is in alignment along the longitudinal axis with the first and second apertures when the rotor is in a first position, and the channel is off-set from the longitudinal axis when the rotor is in a second position. The rotor includes a frontal wall protruding from the opening to the cavity such that the rotational position of the rotor within the cavity is controllable by pressure applied to the frontal wall.

An advantage of the present invention is that it provides a vacuum tubing valve which is inexpensive to manufacture.

Another advantage of the present invention is that it provides a vacuum tubing valve which is disposable.

Another advantage of the present invention is that it provides a vacuum tubing valve which is prevents undesirable backflow.

Another advantage of the present invention is that it provides a vacuum tubing valve for medical and/or dental operations which assists in preventing the transmission of bacteria, diseases and viruses to a patient.

Another advantage of the present invention is that it provides a vacuum tubing valve which can be easily manufactured and assembled.

These and other objects and advantages of the present invention will no doubt become obvious to those of ordinary skill in the art after having read the following detailed description of the preferred embodiment which is illustrated in the various drawing figures.

BRIEF DESCRIPTION OF THE DRAWINGS

FIG. 1 is a perspective view of a vacuum tubing valve assembly of the present invention connected to a saliva ejector tube assembly and vacuum tube illustrated in ghost lines;

FIG. 2 is an exploded view of the vacuum tubing valve assembly of FIG. 1 illustrating a stator unit and a rotor;

FIG. 3 is a cross-sectional view of the vacuum tubing valve assembly, saliva ejector tube assembly and vacuum tubing with the rotor in the "open" position taken along line 3—3 of FIG. 1;

FIG. 4 is a cross-sectional view, similar to FIG. 3, of the vacuum tubing valve assembly, saliva ejector tube assembly and vacuum tubing with the rotor in the "closed" position; and FIG. 5 is a cross-sectional view of the vacuum tubing valve assembly, saliva ejector assembly, vacuum tubing in an alternative embodiment including a vacuum tubing adaptor.

DETAILED DESCRIPTION OF THE PREFERRED EMBODIMENT

FIGS. 1–5 show a vacuum tubing valve of the present invention and referred to by general reference character 10 with FIG. 1 illustrating a saliva ejector tube assembly 12 in ghost lines, and FIGS. 1 and 2 including a vacuum tubing 14 in ghost lines. FIG. 2 illustrates an exploded view of the vacuum tubing valve 10 with a stator unit 16 and rotor 18 separated. The stator unit 16 includes a first receiver cylindrical tubular shoulder 20, extending a length "l" of one and one-eighth an inch from the center of the stator 16 and forming an elongated tubular aperture 22 extending along a longitudinal axis 24. The interior surface diameter "d" of the tubular aperture 22 along the first one-half an inch is 0.26 inches, and the diameter "d" of the remaining length of aperture 22 is 0.213 inches. The saliva ejector tube 12 has an exterior surface diameter "d" of approximately 0.25 inches. One terminal end of the saliva ejector tube assembly 12 is positioned within the aperture 22 with the terminal end abutting a ledge 25, thereby frictionally securing the shoulder 20 and assembly 12. A lateral air inlet aperture 26 of approximately 0.05 inches intersects the narrow section of the aperture 22 beneath the ledge 25 and extends perpendicular to aperture 22.

The stator unit 16 is comprised of a plastic injection-molded material including a first semi-circular disc-shaped wall 30 of a radius "r" of approximately five-eighth an inch joined with a forward rectangular surface of a height "h" of eight-tenths of an inch. A second wall 31, identical to wall 30 is spaced from wall 31 and joined by a C-shaped wall 32 of a width "w" of approximately one-half an inch. An aperture 33 is in the wall 32 and coaxial with the axis 24 to provide a fluid path with the aperture 22. Therefore, the interior of the walls 30, 31 and 32 form a cavity 40 with a partially arcuate interior and an opening about the straight frontal edges of walls 30, 31 and 32.

The stator unit 16 includes a second receiver cylindrical tubular shoulder 42, extending longitudinally 0.25 inches from an aperture 44 in the wall 32 and extending coaxially along the axis 24 for receiving the vacuum tubing 14. The interior and exterior surface diameters of the shoulder 42 are 0.213 and 0.375 inches, respectively. The exterior surface diameter of shoulder 42 is slightly greater than the natural interior surface diameter of the vacuum tubing 14 so that the terminal end of tube 14 may be frictionally secured to shoulder 42. Therefore, apertures 33 and 44 are aligned with the shoulders 20 and 42.

The C-shaped rotor 18 is positioned and rotatable within the cavity 40 about an axis of rotation 51 common to the cavity 40 and the rotor 18. The radius of the rotor 18 is substantially equal to but less than the interior radius "h" of the C-wall 46. The rotor 18 includes a flat frontal wall segment 52 and a frontal wall segment 53 joined at an apex 54 to form a V-shaped frontal wall for engagement by a finger of a human being. The angular displacement "O" of the surfaces 52 and 53 is approximately 155 degrees. The segments 52 and 53 extend over the edges of the walls 30, 31 and 32 so as to form stop members 55 and 56, respectively. Thus, the rotor 18 when in the cavity 40 can rotate approximately 25 degrees responsive to pressure on either of the walls 52 or 53. Thus, the rotor 18 rotates counter clockwise within the cavity 40 of the stator 16 until the stop member 55 contacts the edge of wall 30, 31 or 32. In response to pressure on frontal wall 52, the rotor 18 rotates clockwise within cavity 40 of the stator 16 until stop member 56 contacts the edge of wall 30, 31 or 32.

About the curved edge of the rotor 18 is a rotor C-shaped disc wall 62 extending to the frontal wall segments 52 and 53. The width of the C-shaped disc 62 is substantially less than the interior width of wall 32 and the interior spacing between walls 30 and 31. A cylindrical shape tube 64 forms a radian extending from edge-to-edge of the C-shaped disc 62 and includes a central cylindrical channel 72 which is coaxial with the axis 24 when the stop member 55 abuts the edge of walls 30, 31 or 32. The C-shaped disc wall 62 includes an opening 73 extending laterally through the C-shaped disc wall 62, continuing inside the perimeter of the C-shaped disc wall 62 and along the perimeter of the tube 64. The opening 73 allows two spring-like arms 73A and 73B to be formed. The pliability of the arms 73A and 73B provides flexibility in the disc wall 62 such that as the rotor 18 rotates within the cavity 40 of the stator 16 friction decreases while maintaining contact with the interior wall of the cavity 40. This alleviates need for a lubricant which may otherwise be needed to maintain smooth rotation of the rotor 18. An air inlet passageway 74 one hundredth an inch in diameter extends laterally and intersects the channel 72. The diameter of the channel 72 coincides with that of apertures 22 and 44. The exterior diameter of the tube 64 is substantially equal to the interior width of wall 32 and the interior spacing between walls 30 and 31. Thus, the apex of the tube 64 makes frictional engagement with the inside of the walls 30 and 31 forming the cavity 40.

A partition wall 76 extends from the tube 64 forward to the frontal wall segments 52 and 53. The thickness of the wall 76 is equal to that of the C-shaped disc wall 62. About the peripheral edge of the wall 76 are a pair of lips 77 and 78. Thus a pair of cavities 79 and 80 are formed between the tube 64, frontal wall segments 52 and 53, and the lips 77 and 78. The structure of the rotor 18 is such that it can be produced of plastic.

Within the cavity 40 of the stator 16 and attached to the interior surface of the walls 31 and 32, is a protruding guide member 82. The guide member 82 extends perpendicularly from the walls 31 and 32 adjacent to the rotational path of disc 62 to preclude lateral wobble of the rotor within the cavity 40. The guide 82 projects approximately 0.308 inches from the wall 31. When the stator 16 and the rotor 18 are assembled as in FIGS. 1, 3–5, and pressure is applied about the frontal wall segments 52 or 53, the rotor 18 rotates and the lateral side of arcuate disc 62 rubs alongside the guide 82, thereby assisting in stabilizing rotor 18 during the rotation and when stationary.

When valve assembly 10 is "open" as shown in FIGS. 1, 3 and 5, the segment 53 is pushed with the stop 53 in abutment with walls 30, 31 and/or 32. Then the channel 72 is aligned with the axis 24 to form a continuous channel through aperture 22, channel 72, and aperture 44. Then, when the vacuum tubing valve assembly 10 is utilized, e.g. during dental or medical operations, a first end 90 of the saliva ejector tube assembly 12 is positioned inside a patient's mouth. An air vacuum means creates a force extracting air, saliva and debris from the patient's mouth, through the saliva ejector tube assembly 12, the aperture 22, the channel 72, the aperture 44, the vacuum tubing 14 and then to a reservoir, as illustrated by the arrows in FIG. 1. When the valve assembly 10 is in the "open" position, the air inlet passageway 74 creates an air path increasing the air vacuum pressure.

To obstruct the path, i.e. "close" the valve, pressure is applied to the wall segment 52, and rotating the rotor 50 until the stop member 56 abuts the walls 30, 31 and/or 32, as illustrated in FIG. 4. In this position, the channel 72 is removed from the longitudinal axis 24 and the exterior walls of the partition 64 block flow between the apertures 22 and 44. In such position the exterior apex of the walls of partition 64 are in frictional engagement in the interior surface of walls 30 and 31.

In the "open" position the air inlet 26 and inlet passageway 74 prevent any potential back air pressure from increasing within the first shoulder 20 and saliva ejector tube 12. This resists tendencies of any back pressure from drawing saliva or debris in the shoulder 20 or tube 12 back in to the patient's mouth.

FIG. 5 illustrates an alternative installation embodiment of the present invention. The elements of the assembly are identical to those of FIGS. 1–4 except that a tubing adapter 94 is joined to the shoulder 42. Adaptor 94 includes a first tapered end 96 for receiving the vacuum tubing 14. The exterior surface diameter of the end 96 is less than the interior surface diameter of the vacuum tubing 14 so that a pressure fit is realized. The exterior diameter of the vacuum tubing adapter 94 increases end-to-end from the first end 96 to a second end 98 opposite the first end 96. About the end 98, an opening is formed and in frictional engagement with the exterior of the shoulder 42. The vacuum tubing adapter 94 forms an elongated tubular aperture 99 positioned along the longitudinal axis 24.

The valve assembly 10 is designed such that both the stator 16 and rotor 18 can each be made by a one-shot injection molding procedure. Then, the rotor 18 and stator 16 can be assembled simply by inserting the rotor 18 in the cavity 40. All components may be made from a common plastic material. Pliable tubing may then be attached merely by hand manipulation. Thus, valves 10 are very economical to manufacture, extremely easy 40 to install and use and readily disposable after use in association with a patient.

Although the present invention has been described in terms of the presently preferred embodiments, it is to be understood that such disclosure is not to be interpreted as limiting. Various alternations and modifications will no doubt become apparent to those skilled in the art after reading the above disclosure. Accordingly, it is intended that the appended claims be interpreted as covering all alterations and modifications as fall within the true spirit and scope of the invention.

We claim:

1. A vacuum tubing valve comprising:
   a first receiver tube shoulder (20) extending along a longitudinal axis (24) for receiving a first tubular hose (12);
   a stator unit (16) including a first half-disc shaped wall (30), a second half-disc shaped wall (31) connected parallel to and in alignment with said first half-disc shaped wall (30) by a first C-shaped wall (32) intermediate and perpendicular to said first and second half-disc shaped walls (30, 31) thereby forming a C-shaped cavity (40) with an opening about the side opposite said C-shaped wall (32), a first aperture (33) within said C-shaped wall (32), a second aperture (44) within said first C-shaped wall (32) and in axial alignment with said first aperture (33), the first receiver tube shoulder (20) being joined with said first C-shaped wall (32) about said first aperture (33);
   a second receiver tube shoulder (42) extending along said longitudinal axis (22) and joined to the stator (16) about said second aperture (44); and
   a C-shaped rotor (18) positioned within said cavity (40) and rotatable within said cavity (40), having an elongated channel (72) extending end-to-end, said channel (72) being in alignment along said longitudinal axis (24) and with said first and second apertures (33, 44) when said rotor (18) is in a first position, and said channel (72) is off-set from said longitudinal axis (24) and with said first and second apertures (33, 44) when the rotor (18) is in a second position, a frontal wall (52, 53) protruding from said cavity (40) opening such that the rotational position of the rotor (18) within said cavity (40) is controllable by pressure applied to said frontal wall (52, 53).

2. The valve of claim 1 wherein
   the rotor (18) includes a partition wall (76) parallel with and intermediate said half-disc shaped walls (30, 31) and rotatable within said cavity (40), said partition wall (76) extending to the exterior of said cavity (40) opening and joined to said frontal wall (52, 53).

3. The valve of claim 2 wherein
   the rotor includes a cylindrical shaped tube (64) of a diameter substantially equal to the width of said stator cavity (40) with and in frictional engagement with said first and second rotor C-shaped walls (30, 31) and with said channel extending end-to-end of said tube (64).

4. The valve of claim 3 wherein
   said frontal wall (52, 53) extends beyond said opening of said cavity (40) by a rotational distance of at least twenty degrees relative to the axis of rotation (51) of the rotor (18).

5. The valve of claim 4 wherein
   said frontal wall (52, 53) includes a first and a second stop members (55, 56), said first and second stop members (55, 56) being of a size exceeding a cross-sectional dimension of said cavity (40) with said first or second stop members (55, 56) abutting the rotor (18) in response to pressure to said frontal wall (52, 53), whereby the maximum rotational movement of the rotor (18) within said cavity (40) is limited clockwise and counter-clockwise.

6. The valve of claim 5 wherein
   said first stop member (55) abuts the stator (18) when said channel (72) is coaxially aligned with said first and second apertures (33, 44).

7. The valve of claim 6 wherein
   said second stop member (56) abuts the stator (18) when said channel (72) is not aligned with said first and second apertures (33, 44).

8. The valve of claim 7 wherein
   the rotor (18) further includes C-shaped disc wall (62) extending from said tube (64) to adjacent to the interior surface of said wall (32) and having a radius coinciding With said axis of rotation (51).

9. The valve of claim 8 wherein
   said C-shaped disc wall (62) is of a width coinciding with a width of said partition wall (76).

10. The valve of claim 9 further including
    a guide member (82) within said cavity (40) and protruding from one of said half-disc shaped walls (30, 31) and in frictional engagement with said C-shaped disc (62), whereby said member (82) resists lateral movement of said C-shaped disc (62).

11. The valve of claim 10 wherein
    the rotor (18) includes a first cavity (79) positioned between said tube (64) and said frontal walls (52, 53).

12. The valve of claim 11 wherein
    the rotor (18) includes a second cavity (80) positioned between said tube (64) and said frontal wall (52, 53) with said partition wall (76) intermediate said first and second cavities (79, 80).

13. The valve of claim 12 wherein
    the stator (16) unit is comprised of a plastic injection-molded material.

14. The valve of claim 9 wherein
    said C-shaped disc wall (62) further includes an opening (73) extending laterally through said disc wall (62) continuing inside the perimeter of said disc wall (62) and along the perimeter of said tube (64) to form spring-like arms (73A, 73B) rotatable adjacent to the interior surface of said wall (32).

15. The valve of claim 3 further including
    an air inlet hole (26) in the first receiver tube shoulder (20).

16. The valve of claim 15 wherein
    the air inlet hole (26) intersects and extends perpendicular to said longitudinal axis (24).

17. The valve of claim 16 wherein
    the rotor (18) unit is comprised of a plastic injection-molded material.

18. The valve of claim 15 further including
a saliva ejector tube assembly (12) joined to the first receiver tube shoulder (20) adjacent to the air inlet (26).

19. The valve of claim 18 further including flexible tubing (14) engaged to the second receiver tube shoulder (42).

20. The valve of claim 15 further including
an air inlet channel (74) in the rotor (18) extending laterally and intersecting said elongated channel (72).

* * * * *